United States Patent
Murao et al.

(10) Patent No.: US 7,129,217 B2
(45) Date of Patent: Oct. 31, 2006

(54) AQUEOUS ACRYLAMIDE SOLUTION CONTAINING SACCHARIDE

(75) Inventors: Kozo Murao, Kanagawa (JP); Masaaki Seya, Kanagawa (JP)

(73) Assignee: Dia-Nitrix Co., Ltd., Tokyo (JP)

( * ) Notice: Subject to any disclaimer, the term of this patent is extended or adjusted under 35 U.S.C. 154(b) by 89 days.

(21) Appl. No.: 10/507,376

(22) PCT Filed: Mar. 17, 2003

(86) PCT No.: PCT/JP03/03138

§ 371 (c)(1),
(2), (4) Date: Sep. 21, 2004

(87) PCT Pub. No.: WO03/080680

PCT Pub. Date: Oct. 2, 2003

(65) Prior Publication Data

US 2005/0153421 A1    Jul. 14, 2005

(30) Foreign Application Priority Data

Mar. 22, 2002    (JP) .............................. 2002-081512

(51) Int. Cl.
*A61K 31/70* (2006.01)
*A61K 31/715* (2006.01)
*C07H 3/00* (2006.01)

(52) U.S. Cl. .................. 514/23; 514/54; 536/1.11; 536/123.1; 536/124; 435/129

(58) Field of Classification Search ................ 514/23, 514/54; 536/1.11, 123.1, 124; 435/129
See application file for complete search history.

(56) References Cited

U.S. PATENT DOCUMENTS

| 3,785,921 | A | * | 1/1974 | Ide et al. .................. 162/168.3 |
| 4,661,456 | A | * | 4/1987 | Yamada et al. ............. 435/244 |
| 4,950,748 | A | | 8/1990 | Farrar et al. |
| 6,043,061 | A | * | 3/2000 | Ishii et al. .................. 435/129 |

FOREIGN PATENT DOCUMENTS

| EP | 0 284 367 A2 | 9/1988 |
| JP | 51-86186 | 7/1976 |
| JP | 56-1888 | 1/1981 |
| JP | 56-133307 | 10/1981 |
| JP | 60-153798 | 8/1985 |
| JP | 9-118704 | 5/1997 |
| JP | 10-183497 | 7/1998 |
| JP | 10-316714 | 12/1998 |
| JP | 11-89575 | 4/1999 |
| JP | 2001-81697 | 3/2001 |
| JP | 2001-299376 | 10/2001 |
| WO | WO 03/033716 A1 | 4/2003 |

* cited by examiner

*Primary Examiner*—Leigh C. Maier
*Assistant Examiner*—Michael C. Henry
(74) *Attorney, Agent, or Firm*—Oblon, Spivak, McClelland, Maier & Neustadt, P.C.

(57) ABSTRACT

This invention provides an aqueous solution of acrylamide that is useful as a starting material for high-quality polyacrylamide. Starting materials for polyacrylamide are an aqueous solution of acrylamide containing a saccharide and an aqueous solution of acrylamide containing a saccharide produced with the use of a biocatalyst having nitrile hydratase activity.

27 Claims, No Drawings

AQUEOUS ACRYLAMIDE SOLUTION CONTAINING SACCHARIDE

TECHNICAL FIELD

The present invention relates to an aqueous solution of acrylamide that is useful as a starting material for high-quality polyacrylamide.

BACKGROUND ART

Acrylamide polymers have a wide variety of applications. Examples include use as flocculants, agents for paper manufacturing, soil conditioners, agents for recovering petroleum, thickeners for drilling fluid, and polymer absorbers. An acrylamide polymer is required to have properties such that it has a very high molecular weight, it generates a small amount of water-insoluble matter when dissolved in water, and the like, in order to be put to use in such applications.

A variety of processes have been proposed as processes for obtaining such high molecular weight acrylamide polymer with good solubility. An example of such process is carried out by using a chain transfer agent that prevents polymers with abnormally high molecular weights from being generated or a substance that can prevent crosslinking, which occurs under dry conditions. However, the quality of acrylamide is presumed to significantly affect the quality of the acrylamide polymer. This can be deduced based on the fact that, for example, a variety of processes for producing acrylamide from which impurities such as acrolein or oxazole have been removed have been proposed (for example, JP Patent Publication (Kokai) Nos. 8-157439 A (1996) and 10-7638 A (1998)).

Up to the present, however, there has been no report concerning the influence of a saccharide on the properties of the acrylamide polymer.

In the past, acrylamide used to be produced from acrylonitrile with the use of reduced copper as a catalyst. Recently, a process in which a microbial enzyme is used instead of a copper catalyst has been developed and put to practical use. The process in which a microbial enzyme is used is very effective as an industrial production process since the reaction conditions are moderate, substantially no by-product is generated, and this process can be very simply carried out.

Acrylamide produced with the use of a microbial enzyme generates only small amounts of impurities. Thus, high-quality polyacrylamide that has a very high molecular weight and is free from insoluble impurities can be produced therefrom (JP Patent Publication (Kokai) No. 9-118704 A (1997)). Accordingly, such production process is a major process for producing acrylamide these days.

DISCLOSURE OF THE INVENTION

Acrylamide is a highly toxic substance that is designated as a deleterious substance. In general, the use of an aqueous solution with a high acrylamide content results in the formation of polymers with higher molecular weights and the generation of an aqueous solution of highly viscous polyacrylamide. Recently, it is preferable to decrease the amount of acrylamide used for producing polyacrylamide that is employed in a variety of industries because of the public interest in environmental issues and energy issues. Thus, the demand for the production of highly viscous polyacrylamide from an aqueous solution with a low acrylamide content is increasing. Specifically, an object of the present invention is to provide an acrylamide solution that can provide polyacrylamide with higher viscosity from an aqueous solution with a low acrylamide content and polyacrylamide produced from such acrylamide solution.

The present inventors have conducted concentrated studies in order to attain the above object. As a result, they have found that an aqueous solution of acrylamide containing saccharides can provide an aqueous solution of polyacrylamide with a higher viscosity than that of polyacrylamide obtained from an aqueous solution with an equivalent acrylamide content that contains no saccharide. This has led to the completion of the present invention. They also unexpectedly found that viscosity could be dramatically enhanced with a saccharide content of as low as 100 mg/l or lower, and even 50 mg/l or lower.

Specifically, the present invention relates to:

(1) an aqueous solution of acrylamide containing saccharide;

(2) an aqueous solution of acrylamide containing 0.1 mg to 100 mg of saccharide per liter thereof;

(3) an aqueous solution of acrylamide containing 1.0 mg to 50 mg of saccharide per liter thereof;

(4) an aqueous solution of acrylamide containing 3.0 mg to 19 mg of saccharide per liter thereof;

(5) the aqueous solution of acrylamide containing saccharide according to any of (1) to (4), which further comprises saccharide-containing solution prepared with the use of a cultured organism;

(6) the aqueous solution of acrylamide containing saccharide according to (5), wherein the organism expresses nitrile hydratase;

(7) the aqueous solution of acrylamide containing saccharide according to (6), wherein the organism that expresses nitrile hydratase is a microorganism;

(8) the aqueous solution of acrylamide containing saccharide according to (7), wherein the microorganism is of the genus *Rhodococcus*;

(9) the aqueous solution of acrylamide containing saccharide according to (8), wherein the microorganism of the genus *Rhodococcus* is *Rhodococcus rhodochrous*;

(10) the aqueous solution of acrylamide containing saccharide according to any one of (1) to (9), which is produced with the use of a biocatalyst having nitrile hydratase activity;

(11) An acrylamide polymer containing a saccharide, wherein the viscosity of a polyacrylamide solution obtained from the aqueous solution of acrylamide containing a saccharide according to any one of (1) to (10) is higher than that of a polyacrylamide solution obtained from an aqueous solution of acrylamide consisting of acrylamide dissolved in water to have the same acrylamide content as said aqueous solution containing saccharide;

(12) a polyacrylamide polymer obtained from the aqueous solution of acrylamide containing saccharide according to any one of (1) to (11); and

(13) a process for producing an aqueous solution of acrylamide containing saccharide, wherein acrylamide is produced with the use of a biocatalyst that has nitrile hydratase activity and contains saccharide.

Hereinafter, the present invention is described in detail.

The term "aqueous solution of acrylamide" used in the present invention refers to an aqueous solution wherein acrylamide accounts for 40% to 60% by mass, and preferably 50% by mass, of such solution. When a polymerization initiator such as ammonium persulfate is added to the aqueous solution of acrylamide, acrylamide is polymerized, and an aqueous solution of polyacrylamide is then generated.

The term "saccharide" used herein refers to saccharide that can be detected by the phenol-sulfuric acid method. Examples thereof include monosaccharide, polysaccharides, and mixtures thereof, which generate furfural or a furfural derivative with the aid of sulfuric acid. Polysaccharides include glycoconjugates, such as glycoproteins and glycolipids. Saccharides may be produced by a method in which a biocatalyst such as an enzyme is employed or by chemical synthesis. Alternatively, saccharides may be produced from organisms or separated from biomaterials.

The term "a saccharide-containing solution prepared with the use of an organism" refers to a solution containing saccharide produced from an organism. Examples of a saccharide-containing solution prepared with the use of an organism include a supernatant obtained via centrifugation of a suspension of organisms such as cultured microorganisms and a solution prepared from the aforementioned supernatant via purification or other means. The aqueous solution of acrylamide containing a saccharide-containing solution of the present invention can be obtained by adding a saccharide-containing solution prepared from organisms to an aqueous solution of acrylamide. When the content of the saccharide produced from organisms is low, saccharides may be adequately added to adjust the saccharide content in the aqueous solution of acrylamide.

The term "organisms" used herein includes all types of organisms such as isolated animals, plants, and microorganisms. The organisms further include cells isolated from animals or plants, established cell lines derived from animals or plants, isolated microorganisms, and organelles thereof. These organisms may naturally occur or may be artificially and genetically modified.

The saccharide content according to the present invention is represented in terms of glucose that is measured by the phenol-sulfuric acid method. The method for measurement according to the phenol-sulfuric acid method is described in detail in, for example, *Kiso Sekagaku Jikken Hou* (Basic technique for biochemical experimentation), vol. 5, p. 118 (the Japanese Biochemical Society (ed.)). Specifically, the value is obtained based on a calibration curve prepared based on the glucose density and the absorbance using glucose. The "phenol-sulfuric acid method" employed herein is carried out in accordance with the aforementioned *Kiso Sekagaku Jikken Hou* (Basic technique for biochemical experimentation), vol. 5, p. 118 (the Japanese Biochemical Society (ed.)). The details thereof are described below.

(i) Phenol (special grade) and distilled water are used to prepare an aqueous solution that are 5% phenol by mass. (ii) A sample solution (1 ml) is placed in a 16.5 mm-test tube, 1 ml of the solution obtained in (i) is added thereto, and they are thoroughly mixed. (iii) Concentrated sulfuric acid (5 ml, special grade) is quickly added thereto, and the tube is agitated while mixing the contents thereof for 10 minutes. (iv) The tube is allowed to stand at room temperature for 20 minutes, and the absorbance at 490 nm is measured. From thus-determined absorbance, the saccharide content in the sample solution is determined in terms of glucose on the basis of a calibration curve prepared with glucose.

In the present invention, the minimal saccharide content in the aqueous solution of acrylamide is preferably 0.1 mg/l, more preferably 1 mg/l, and particularly preferably 3 mg/l. The maximal content is preferably 100 mg/l, more preferably 50 mg/l, and particularly preferably 19 mg/l. A higher content is preferable for sufficiently increased viscosity. When a large amount of saccharides is contained, however, an aqueous solution of acrylamide or an acrylamide polymer produced therefrom may disadvantageously develop color. Accordingly, an excessively high saccharide content is not preferable for applications that disfavor such color development, from the viewpoint of quality.

A biocatalyst that has the nitrile hydratase activity of the present invention includes an organism that naturally or artificially has nitrile hydratase activity, a processed product thereof, and nitrile hydratase itself. In this case, an organism is preferably a microorganism. Examples of a microorganism that can express nitrile hydratase include those belonging to the genera *Bacillus, Bacteridium, Micrococcus, Brevibacterium, Corynebacterium, Nocardia, Pseudomonas, Rhodococcus*, and *Microbacterium* and the *Rhodococcus rhodochrous* strain.

Also, an organism in which a naturally- or artificially-modified nitrile hydratase gene has been artificially incorporated and expressed or nitrile hydratase isolated therefrom (which may be thoroughly or roughly purified) can be presently used in the present invention.

An organism and a processed product thereof include those that have been subjected to washing or treatment with an agent according to need, fractured products thereof, and those immobilized via entrapment, crosslinking, or carrier-binding.

The "biocatalyst" used in the present invention include an organism such as the aforementioned microorganism, a suspension containing such organism, and a processed product thereof.

The use of a biocatalyst that has nitrile hydratase activity enables the production of acrylamide by a very simple process at the industrial level. Specifically, acrylamide can be produced without the use of reduced copper as a catalyst under moderate reaction conditions, while generating substantially no by-product.

The "aqueous solution of acrylamide containing 0.1 mg to 100 mg of saccharide per liter thereof" according to the present invention can be produced in the following manner.

Acrylamide (500 mg) is dissolved in distilled water to prepare 1 liter of aqueous solution of acrylamide. An aqueous solution of saccharide is added thereto to bring the saccharide content to 0.1 mg to 100 mg per liter of aqueous solution of acrylamide in terms of glucose determined via the phenol-sulfuric acid method. Thus, the aforementioned aqueous solution of acrylamide can be obtained. In this case, the amount of acrylamide to be dissolved may be varied within the range of 400 g to 600 g, and the acrylamide content in the final aqueous solution may be adjusted at 40% to 60% by weight. Purified or unpurified saccharide may be added. Commercialized acrylamide may be used. Alternatively, the aqueous solution of acrylamide produced from acrylonitrile with the use of a biocatalyst, with or without purification, may also be used, in which acrylamide content is adjusted to 40% to 60% by weight.

When the aforementioned aqueous solution of acrylamide containing saccharide is produced from acrylonitrile with the use of a biocatalyst, the saccharide content in the biocatalyst is assayed, the biocatalyst is added in such a manner that the content thereof becomes 0.1 mg to 100 mg per liter of the aqueous solution of acrylamide after the reaction, and acrylonitrile is brought into contact with the biocatalyst to initiate the reaction. The saccharide in a biocatalyst refers to saccharide in a liquid containing a biocatalyst, such as a microorganism, suspended therein or that in a liquid containing a biocatalyst immobilized on a carrier or the like immersed therein. More specifically, saccharide can be obtained by bringing starting materials, i.e., acrylonitrile and water, into contact with a biocatalyst containing saccharide in a reaction chamber at 0° C. to 90°

C., and preferably 5° C. to 50° C. An inhibitor of polymerization, a stabilizer for a catalyst, or the like can be added to the reaction solution or a suspension of a biocatalyst according to need. The reaction may be carried out using a fixed bed, moving bed, fluidized bed, stirred tank, or any other reactor, and it may be carried out via a batch or continuous process. An aqueous solution of saccharide may be added to the reaction chamber in such a manner that the saccharide content in terms of glucose determined via the phenol-sulfuric acid method becomes 0.1 mg to 100 mg per liter of the aqueous solution of acrylamide after the reaction to allow the biocatalyst to react with acrylonitrile in the reaction chamber.

The thus obtained aqueous solution of acrylamide can be subjected to a process of purification, depending on the application thereof. Examples of a process for purification thereof include filtration through a filter (JP Patent Publication (Kokoku) No. 5-49273 B (1993)) and purification with the aid of air bubbles (JP Patent Application No. 11-254151).

The thus obtained aqueous solution of acrylamide can be used as a starting material to obtain an aqueous solution of polyacrylamide in the same manner as with the conventional method for acrylamide polymerization. Thus, the aqueous solution of polyacrylamide obtained from the aqueous solution of acrylamide of the present invention has a viscosity higher than that of an aqueous solution of polyacrylamide obtained from an aqueous solution of acrylamide with the same acrylamide content but containing no saccharide. Such aqueous solution of polyacrylamide can be utilized in various applications, such as in a flocculent, an agent for paper manufacturing, a soil conditioner, an agent for recovering petroleum, a thickener for drilling fluid, and a polymer absorber, as an acrylamide polymer. Accordingly, the polyacrylamide polymer obtained from the aqueous solution of acrylamide of the present invention is also within the scope of the present invention.

The properties of the resulting aqueous solution of polyacrylamide can be evaluated by, for example, measuring the viscosity of the polymer using a viscometer. Specifically, the properties can be evaluated by measuring the viscosity using a B-type viscometer in accordance with a conventional technique.

This description includes part or all of the contents as disclosed in the description and/or drawings of Japanese Patent Application No. 2002-081512, which is a priority document of the present application.

BEST MODES FOR CARRYING OUT THE INVENTION

The present invention is described in greater detail with reference to the following examples, although the technical scope of the present invention is not limited thereto.

Example 1 and Comparative Example 1 independently describe the case of polyacrylamide prepared from a commercialized aqueous solution of acrylamide. Example 2 and Comparative Example 2 independently describe the case of polyacrylamide prepared from acrylamide produced from acrylonitrile with the use of a biocatalyst containing saccharide.

EXAMPLE 1

[Preparation of a Saccharide-Containing Solution)

The *Rhodococcus rhodochrous* J1 strain (deposited as of Sep. 18, 1987, under the accession number: FERM BP-1478 (the original deposit) at the National Institute of Bioscience and Human-Technology, the Agency of Industrial Science and Technology (presently the International Patent Organism Depositary of the National Institute of Advanced Industrial Science and Technology (Tsukuba Central 6, 1-1-1 Higashi, Tsukuba, Ibaraki, Japan))) was subjected to aerobic culture in a medium (pH 7.0) that was 2% glucose, 1% urea, 0.5% peptone, 0.3% yeast extract, and 0.05% cobalt chloride ("%" is by mass) at 30° C. The culture product was filtered though a polysulfone membrane filter (pore diameter 0.1 µm, Kuraray Co., Ltd.), continuously washed with a 50 mM phosphate buffer (pH 7.0), the amount of which was 5 times larger than that of the culture solution, and concentrated to a cell density of 10% on a dry basis. Thus, a cell suspension was obtained.

This cell suspension was placed in a 50-ml centrifuging tube, and subjected to centrifugation at 15,000×g for 30 minutes. The obtained supernatant was used as a saccharide-containing solution.

Measurement of the Saccharide Content in a Saccharide-Containing Solution

The saccharide content in the resulting saccharide-containing solution was measured by the phenol-sulfuric acid method in the following manner.

(i) Phenol (special grade) and distilled water were used to prepare an aqueous solution that was 5% phenol by mass. (ii) A solution (diluted 1,000-fold, 1 ml) was placed in a 16.5 mm-test tube, 1 ml of the solution obtained in (i) was added thereto, and they were thoroughly mixed. (iii) Concentrated sulfuric acid (5 ml, special grade) was quickly added thereto, and the tube was agitated while mixing the contents thereof for 10 minutes. The tube was allowed to stand at room temperature for 20 minutes, and the absorbance at 490 nm was measured. Separately, the calibration curves were prepared using aqueous glucose solutions that were adjusted at 2 mg/l, 10 mg/l, 50 mg/l, and 100 mg/l, respectively, and the saccharide contents of the saccharide-containing solutions were determined based on the calibration curves. As a result, the saccharide content was found to be 15,000 mg/l. The saccharide contained in the saccharide-containing solution is, not limited in theory, deduced to be a polysaccharide produced from cells. Preparation of an aqueous solution of acrylamide containing saccharide Four separate aqueous solutions of 50% acrylamide by mass (1 liter each, Mitsubishi Rayon Co., Ltd.) were provided, and 0.07 ml, 0.2 ml, 3 ml, and 4 ml of the prepared saccharide-containing solutions were independently added to each thereof to prepare aqueous solutions of acrylamide containing saccharides. Each thereof was designated as Example 1-1, 1-2, 1-3, and 1-4.

Preparation of an Aqueous Solution of Polyacrylamide

The prepared aqueous solution of acrylamide containing saccharide was diluted with distilled water to bring the acrylamide concentration to 15% by mass. After adjusting the pH level of the solution to 6.1, the flask was incubated in a water bath at 30° C. while agitating. While replacing the air in the gas phase with nitrogen, 180 mg/l each of ammonium persulfate and sodium bisulfite were added to initiate polymerization. At the same time, the temperature in the water bath was adjusted to 80° C. Approximately 1 hour later, the inside of the water bath was cooled to 25° C. with ice.

Evaluation of Properties of an Aqueous Solution of Polyacrylamide

The viscosity of the resulting aqueous solution was measured using a B-type viscometer (No. 4 Rotor, 6 rpm, 25° C.). The results are shown in Table 1. The hue was visually observed. The colorless solution is represented by "⊙"; the subtly yellowish solution is represented by "○"; the slightly yellowish solution is represented by "Δ"; and the yellowish solution is represented by "×."

COMPARATIVE EXAMPLE 1

An aqueous solution of polyacrylamide was prepared in the same manner as in Example 1, except for the use of an aqueous solution that was 50% acrylamide by mass (Mitsubishi Rayon Co., Ltd.) to which a saccharide-containing solution had not been added. The properties of the resulting aqueous solution of polyacrylamide were evaluated. The results are shown in Table 1.

TABLE 1

|  | Saccharide content | Viscosity of aqueous polymer solution | Hue |
|---|---|---|---|
| Example 1-1 | 1 mg/l | 130,000 mPa · s | ⊙ |
| Example 1-2 | 3 mg/l | 150,000 mPa · s | ⊙ |
| Example 1-3 | 45 mg/l | 200,000 mPa · s | ○ |
| Example 1-4 | 60 mg/l | 220,000 mPa · s | Δ |
| Comparative Example 1 | 0 | 60,000 mPa · s | ⊙ |

EXAMPLE 2

Production of Acrylamide from Acrylonitrile with the Use of a Microbial Enzyme

An aqueous solution of 0.2 g/l sodium acrylate (3,130 g) was added to a jacketed separable flask (internal volume: 5 liters), and 10 g of the cell suspension (containing about 10,000 mg/l of saccharide) obtained in the "Preparation of a saccharide-containing solution" in Example 1 was added thereto. The content of the flask was agitated with two flat rotor blades (blade length: 120 mm, blade width: 20 mm) at 80 rpm while regulating the conditions at a pH level of 7.0 and a temperature of 20° C. Acrylonitrile (Mitsubishi Rayon Co., Ltd.) was continuously fed to maintain the acrylonitrile concentration at 2% by mass. Feeding of acrylonitrile was stopped when the acrylamide concentration became 47%, and the reaction was continued until the amount of remaining acrylonitrile became 0.005% or lower. Cells were removed from this solution through a polyethylene hollow fiber membrane (Sterapore H, pore diameter 0.1 μm, Mitsubishi Rayon Co., Ltd.). Thus, 5 kg of reaction solution of 50% -by-mass acrylamide was obtained.

Measurement of the Saccharide Content in a 50% -by-Mass Solution of Acrylamide

The saccharide content in the resulting aqueous solution that was 50% acrylamide by mass was measured in the same manner as in the "Measurement of the saccharide content in a saccharide-containing solution" in Example 1. When converting the values in terms of glucose, however, a solution prepared by dissolving a known amount of glucose in an aqueous solution that was 50% acrylamide by mass prepared from commercialized acrylamide powder (Wako Pure Chemical Industries, Ltd.) was used. As a result, the saccharide content was found to be 19 mg/l.

Evaluation of Properties of an Aqueous Solution of Polyacrylamide

An aqueous solution of polyacrylamide was prepared from the resulting aqueous solution of acrylamide in the same manner as in Example 1. The properties of the resulting solution were evaluated.

As a result, the viscosity of the solution was found to be 190,000 mPa·s.

All publications, patents, and patent applications cited herein are incorporated herein by reference in their entirety.

INDUSTRIAL APPLICABILITY

The present invention can provide a high-quality aqueous solution of acrylamide that can be a starting material for high-performance polyacrylamide with excellent properties and an aqueous solution of polyacrylamide that can provide high performance at a low concentration.

The invention claimed is:

1. An aqueous solution comprising 40% to 60% by mass of acrylamide and 0.1 mg to 100 mg of saccharide per liter thereof.

2. The aqueous solution as claimed in claim 1 wherein said saccharide is present at from 1.0 mg to 50 mg per liter thereof.

3. An aqueous solution as claimed in claim 1 wherein said saccharide is present at from 3.0 mg to 19 mg of saccharide per liter thereof.

4. The aqueous solution as claimed in claim 1, which is prepared by adding a saccharide-containing solution prepared with the use of a cultured organism to an aqueous solution comprising acrylamide.

5. The aqueous solution as claimed in claim 4, wherein the organism is an organism that expresses nitrile hydratase.

6. The aqueous solution as claimed in claim 5, wherein the organism that expresses nitrile hydratase is a microorganism.

7. The aqueous solution as claimed in claim 6, wherein the microorganism is of the genus *Rhodococcus*.

8. The aqueous solution as claimed in claim 7, wherein the microorganism of the genus *Rhodococcus* is *Rhodococcus rhodochrous*.

9. The aqueous solution as claimed in claim 1, which is produced with the use of a biocatalyst having nitrile hydratase activity.

10. An aqueous solution as claimed in claim 1, which further comprises a polyacrylamide obtained by polymerizing the acrylamide.

11. A process for producing an aqueous solution as claimed in claim 1 comprising producing acrylamide from acrylonitrile in an aqueous solution with the use of a biocatalyst that has nitrile hydratase activity in the presence of a saccharide, and optionally further adding saccharides, such that the resulting aqueous solution contains 40% to 60% by mass of acrylamide and 0.1 mg to 100 mg of saccharides per liter thereof.

12. A process for preparing a polyacrylamide comprising:
   preparing an aqueous acrylamide solution comprising 40% to 60% by mass of acrylamide and 0.1 mg to 100 mg of saccharide per liter thereof, and
   polymerizing the acrylamide in said aqueous acrylamide solution.

13. The process as claimed in claim 12, wherein said polymerizing of the acrylamide is performed by adding a polymerization initiator to said aqueous acrylamide solution.

14. The process as claimed in claim 12, wherein said polymerizing of the acrylamide provides a polyacrylamide having an increased viscosity.

15. The process as claimed in claim 14, wherein said increased viscosity is 130000 mPas to 220000 mPas.

16. The process as claimed in claim 12, wherein said preparing of the aqueous acrylamdie solution is performed by adding a saccharide-containing solution prepared with use of a cultured organism to an aqueous solution comprising acrylamdie.

17. The process as claimed in claim 12, wherein said saccharide is a polysaccharide.

18. The process as claimed in claim 16, wherein said organism is an organism that expresses nitrile hydratase.

19. The process as claimed in claim 18, wherein said organism that expresses nitrile hysratase is a microorganism.

20. The process as claimed in claim 19, wherein said microorganism is of the genus *Rhodococcus*.

21. The process as claimed in claim 20, wherein said microorganism of the genus *Rhodococcus* is *Rhodococcus rhodochrous*.

22. The process as claimed in claim 12, wherein said preparing of the aqueous acrylamide solution is performed by producing acrylamide from acrylonitrile in an aqueous solution with the use of a biocatalyst that has nitrile hydratase activity in the presence of saccharide, and optionally adding saccharides, such that the resulting aqueous solution contains 40% to 60% by mass of acrylamide and 0.1 mg to 100 mg of saccharides per liter thereof.

23. The process as claimed in claim 22, wherein said biocatalyst is an organism that expresses nitrile hydratase.

24. The process as claimed in claim 23, wherein said organism is a microorganism.

25. The process as claimed in claim 24, wherein said microorganism is of the genus *Rhodococcus*.

26. The process as claimed in claim 25, wherein said microorganism of the genus *Rhodococcus* is *Rhodococcus rhodochrous*.

27. The polyacrylamide as claimed in claim 10, which has a viscosity of 130000 mPa·s to 220000 mPa·s.

* * * * *